(12) United States Patent
Jiang et al.

(10) Patent No.: US 7,252,941 B2
(45) Date of Patent: Aug. 7, 2007

(54) EXPRESSION PROFILING BASED ON HISTOCULTURES

(75) Inventors: Ping Jiang, San Diego, CA (US); Mingxu Xu, La Jolla, CA (US); Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 395 days.

(21) Appl. No.: 10/712,781

(22) Filed: Nov. 12, 2003

(65) Prior Publication Data

US 2004/0229234 A1 Nov. 18, 2004

Related U.S. Application Data

(60) Provisional application No. 60/425,945, filed on Nov. 12, 2002.

(51) Int. Cl.
*C12Q 1/68* (2006.01)
(52) U.S. Cl. .................. 435/6; 435/91.51; 435/378
(58) Field of Classification Search .................. None
See application file for complete search history.

(56) References Cited

U.S. PATENT DOCUMENTS 5,474,909 A 12/1995 Connors et al.
5,726,009 A 3/1998 Connors et al.
5,849,579 A 12/1998 Li .............................. 435/325
6,203,984 B1 3/2001 Hu et al.

FOREIGN PATENT DOCUMENTS

WO WO-95/01455 1/1995

OTHER PUBLICATIONS

Singh et al., Head and Neck (2002) 24:437-442.
International Search Report for PCT/US03/36238, mailed on Jan. 7, 2005, 5 pages.
Sgroi et al., Cancer Research (1999) 59:5656-5661.
Yates et al., Experimental Cell Research (2001) 265:203-211.
Furukawa et al., Clinical Cancer Research (1995) 1(3):305-311.
Supplementary Partial European Search Report for EP 03789749.3, mailed on Jul. 13, 2006, 5 pages.

*Primary Examiner*—James Ketter
(74) *Attorney, Agent, or Firm*—Morrison & Foerster LLP

(57) ABSTRACT

Methods of obtaining faithful expression libraries from tissue samples comprise extraction of RNA from intact tissue cultured in three-dimensional sponge-gel based histocultures.

7 Claims, No Drawings

EXPRESSION PROFILING BASED ON HISTOCULTURES

CROSS-REFERENCE TO RELATED APPLICATIONS

This application claims benefit under 35 U.S.C. § 119(e) to U.S. Ser. No. 60/425,945 filed 12 Nov. 2002. The contents of that application are incorporated herein by reference.

TECHNICAL FIELD

The invention relates to preparation of samples, especially tumor samples, as sources of mRNA for expression analysis.

BACKGROUND ART

There is an extensive history of the use of histocultured tumor samples for use in prognosis of tumor development and as a tool for predicting responsiveness to drugs. These histochemical techniques, which are the basis of histoculture drug response assay (HDRA™), have an extensive literature. The general features of this technique are described, for example, in a recent paper by Singh, B., et al., *Head and Neck* (2002) 24:437-442. As described in this paper, briefly, biopsied tissue is washed and cut into 1 to 2 mm³ fragments and placed onto 0.5 cm² pieces of collagen sponge-gel (Gel Foam, Pharmacia & Upjohn, Inc.) in equal quantities. The sponge-gel cultures are then placed into DMEM/Ham's F12 medium with 10% fetal calf serum and gentamicin (50 µg/ml). The cultures are then incubated for 24 hours at 37° C. and 5% $CO_2$. Modifications of this technique are also permissible, provided the three-dimensional nature of the sample is preserved.

It has now been found that in addition to their usefulness as prognostic and drug-screening tools, such cultures are also useful as sources for messenger RNA as a substrate for expression profiling. This is significant in view of the problems associated with providing reliable expression libraries, in particular when derived from patient samples where extraction of high-quality, non-degraded RNA is difficult in view of the necrotic areas present in tumors and in view of the need to transport tumor tissue from a treatment or diagnosis center to a laboratory capable of performing the profiling analysis. By maintaining non-necrotic portions of the tumor in a three-dimensional histoculture, the expression profile of the tumor in situ is effectively preserved.

DISCLOSURE OF THE INVENTION

The invention provides a method to prepare an mRNA library characteristic of expression for use in profiling tissue, especially tumor tissue, in order to characterize the nature of the tissue. In the case of tumor analysis, this profile is helpful in designing treatment, especially in comparison with historical samples with similar expression patterns whose responsiveness to certain protocols is known. Other uses of characteristic expression profiles as related to particular tissue sources will be apparent to the skilled artisan.

Thus, in one aspect, the invention is related to a method to prepare RNA characteristic of a tissue expression which method comprises, after culturing an intact tissue sample in sponge-gel three-dimensional culture, extracting RNA from said culture.

The messenger RNA extracted can then be analyzed using any art recognized technique, such as Northern blot. Preferably, however, the extracted mRNA is used as a template to prepare a cDNA library which can then be analyzed using recognized array techniques, such as those based on Gene-Chips. In other aspects, the invention is directed to mRNA, cDNA and cRNA libraries prepared by the method of the invention and to methods to utilize these libraries for prognosis and treatment selection.

MODES OF CARRYING OUT THE INVENTION

The present invention solves the problem of adequately preserving tissue samples, especially tumor tissue samples, for expression profiling. Presently, biopsied samples are subject to RNA degradation and alteration in expression patterns in the interval between the biopsy and the extraction of RNA for analysis. By maintaining the tissue intact in three-dimensional histoculture, the accuracy of the expression profile is preserved and the degradation of RNA is minimized.

In the method of the invention, the tissue is biopsied using conventional techniques, and then divided into intact portions of the approximate dimension of 1 mm³. Some variation in sample size is, of course, permitted and, for example, pieces in the range of 0.25 mm³-5 mm³, 0.5-3 mm³, preferably 1-2 mm³ are used. The intact tissue piece is then placed into a three-dimensional histoculture, typically by combining the intact sample with a collagen sponge-gel, such as those described in Singh, B., et al., (supra) and multiple additional papers, reviewed, e.g., by Hoffman, R. M., et al., *Int'l J. Oncol.* (1992) 1:467-474; Hoffman, R. M., in *Encyclopedia of Life Sciences* (2001) Nature Publishing Group, London., and generally known in the art in the practice of HDRA™. The collagen-type sponge-gel useful in the invention methods are used as a support for the tissue and thus the dimension of the sponge-gel is substantially greater than the dimension of the fragment; typically, the surface area of the sponge-gel is roughly twice the diameter of the intact tissue sample. The three-dimensional culture is then maintained in suitable medium, such as the media described in the attached publications. The culture is maintained for as long as necessary to preserve the sample for RNA extraction.

RNA extraction is carried out using techniques standard in the art.

The tissue sample that is the source of the expression library is typically tumor tissue. Thus, the invention method is particularly useful in assessing expression profiles for tumors of the breast, lung, colon, liver, stomach, pancreas, prostate, head and neck, ovary, and brain. This list is non-exhaustive, as any solid tumor or, indeed, any tissue may be used as the source of the library.

The extracted RNA is then analyzed according to the needs of the investigator. Northern blot techniques may be used, but additional information can be obtained using commercially available expression arrays, for example, expression arrays now available from Affymetrix. Approximately 15 µg of labeled cDNA is required. Typically, the extracted RNA is converted into cDNA by reverse transcription, most generally by priming with an oligo-dT primer coupled to the T7 RNA polymerase promoter. The resulting single-stranded cDNA is converted to double-stranded DNA which thus produces a template suitable for T7 polymerase-driven in vitro transcription (IVT). Labeled nucleotides are incorporated during the in vivo transcription to permit later detection of the resulting cRNA. The resulting transcription product, cRNA, is then used to provide the profile as detected by DNA arrays supplied on chips.

In the latter determination, the labeled cRNA is fragmented by heating in Mg++ containing buffer and combined in a hybridization cocktail containing salmon sperm DNA, BSA and spiked control RNA's. Approximately 250 μl of cocktail is applied to GeneChips™ and hybridized for 16 hours at 50° C. as described in the *Affymetrix Gene Chip Expression Analysis Technical Manual* (2001). As there described, after hybridization, the chips are taken through high and low stringency washes followed by staining with phycoerythrin-labeled streptavidin (molecular probes) antibody amplification with biotinylated anti-streptavidin antibody (Vector Labs) and an additional staining with phycoerythrin labeled streptavidin. After further washing, the arrays are digitized in an Affeymetrix scanner and the images evaluated using Microarray Suite 5™ software.

The foregoing description is merely exemplary of the variety of techniques that could be used to analyze the RNA extracted from the culture according to the method of the invention.

The data obtained from the determination of the components of the library can be used effectively to predict outcomes for subjects from whom tumor tissue is removed and analyzed according to the invention method, and can also be used to design protocols for treatment, as well as to predict chemosensitivity.

The invention claimed is:

1. A method to prepare an expression profile of a tissue which method comprises the step of extracting RNA from an intact sample of said tissue cultured using a three-dimensional collagen sponge-gel culture.

2. The method of claim 1, which further includes subjecting said RNA to analysis to obtain expression data.

3. The method of claim 1, which further includes converting the extracted RNA into cDNA.

4. The method of claim 3, which further includes preparing labeled cRNA from said cDNA and
analyzing said cRNA using microarray analysis.

5. The method of claim 1, wherein said tissue is tumor tissue.

6. The method of claim 5, wherein said tumor is of the breast, lung, colon, liver, stomach, pancreas, prostate, head, neck, ovary, or brain.

7. The method of claim 2, which further includes preparing a prognosis based on said data.

* * * * *